United States Patent [19]

Yokozeki et al.

[11] Patent Number: 4,650,759
[45] Date of Patent: Mar. 17, 1987

[54] METHOD OF PRODUCING L-CARNITINE

[75] Inventors: Kenzo Yokozeki; Koji Kubota, both of Kawasaki, Japan

[73] Assignee: Ajinomoto Company, Incorporated, Tokyo, Japan

[21] Appl. No.: 599,923

[22] Filed: Apr. 13, 1984

[30] Foreign Application Priority Data

Apr. 13, 1983 [JP] Japan ................................. 58-65009

[51] Int. Cl.⁴ ......................... C12P 13/00; C12P 7/40; C12P 7/42
[52] U.S. Cl. .................................... 435/128; 435/132; 435/146
[58] Field of Search ............... 435/128, 129, 132, 146, 435/170, 178, 106, 877; 260/501.13; 568/844

[56] References Cited

U.S. PATENT DOCUMENTS 4,221,869 9/1980 Vandecasteele et al. ............ 435/877
4,371,618 2/1983 Cavazza ............................... 435/128
4,413,142 11/1983 Fiorini et al. ........................ 568/844

OTHER PUBLICATIONS

Seim, H. et al., (1982) Acta. Biol. Med. Ger. vol. 42(4), pp. 379–389 (abst.).
Chem. Abst. vol. 98, 1983, 122,551z.

Primary Examiner—Charles F. Warren
Assistant Examiner—Janet M. Dougherty
Attorney, Agent, or Firm—Oblon, Fisher, Spivak, McClelland & Maier

[57] ABSTRACT

A method for producing L-carnitine which involves contacting crotonbetaine or a non-toxic, soluble salt of this compound with a microorganism or an enzyme fraction of this microorganism which is capable of converting crotonbetaine or its salts into L-carnitine. The conversion is conducted in an aqueous medium under conditions suitable for production of L-carnitine.

6 Claims, No Drawings

METHOD OF PRODUCING L-CARNITINE

BACKGROUND OF THE INVENTION

1. Field of the Invention

The present invention relates to a method for producing L-carnitine. It is known that L-carnitine occurs usually in living bodies and it accelerates the growth of children.

2. Description of the Prior Art

As methods for producing directly L-carnitine, a French Patent Application No. 7722183 and a Japanese Patent Laid-Open No. 39731/1982 are known. The method of French Patent Application No. 7722183 employs NAD and it requires a treatment to enable NAD to pass through the cell wall, so that it leads to an increase in cost. Further, in the method of Japanese Patent Laid-Open No. 39731/1982, the reaction requires 2-oxoglutamic acid, a reducing agent, ferrous ions, catalase and the like in addition to $\beta$-butylobetaine that is the substrate, so that the reaction system becomes complicated, from which an increase in cost results.

SUMMARY OF THE INVENTION

The inventors researched to find an effective method as compared with the above-mentioned conventional methods, and as a result they have found a novel method for solving at once the present technical and economical problems.

The invention is a method for producing L-carnitine characterized in that crotonbetaine is transformed into L-carnitine in an aqueous medium by the action of microorganisms competent to transform crotonbetaine into L-carnitine.

By a microorganism competent to transform crotonbetaine into L-carnitine is meant a microorganism which, when brought into contact with crotonbetaine under the conditions hereinafter described, produces L-carnitine by the action of enzymes contained in the microorganism on the substrate crotonbetaine. It is sufficient to bring crotonbetaine into contact with the whole microorganism cells, culture broth, or treated cells of the microorganism. Furthermore, since certain enzymes in the microorganism bring about the transformation of crotonbetaine into L-carnitine, any fraction of the microorganism which contains these enzymes may be used in the method of this invention.

In the method of this invention, any of various salts of crotonbetaine may be substituted for crotonbetaine itself. The requirements of the salt used are that it be soluble in the aqueous medium employed and that it be non-toxic to the microorganism used. By non-toxic it is meant that the salt does not retard the growth or metabolism of the microorganism, nor does it inhibit the action of the enzymes of the microorganism which bring about the transformation of crotonbetaine into L-carnitine. Salts which may be used by the method of this invention include: sulfate, hydroxide, chloride, bromide, and phosphate. Of these, the most preferred is sulfate.

The determination of whether a microorganism is competent for the transformation of crotonbetaine into L-carnitine is a routine matter which could easily be made by anyone skilled in the art. The procedure entails allowing a microorganism which has not previously been determined to produce L-carnitine from crotonbetaine to come into contact with crotonbetaine in an aqueous medium, such as a medium described in the examples, given later in this specification, followed by analysis, as defined in the examples, to determine the presence of L-carnitine and the quantity produced. The present invention lies in the use of the substrate crotonbetaine and salts thereof as a precursor to L-carnitine, a heretofore unknown precursor for transformation into L-carnitine.

DESCRIPTION OF THE PREFERRED EMBODIMENTS

The microorganisms used in the present invention and competent to transform crotonbetaine into L-carnitine include, for example, the following ones:

Alcaligenes marshallii: ATCC 21030
Acinetobacter lwoffi: ATCC 9036
Aglobacterium tumefaciens: ATCC 4452
Arthrobacter paraffineus: ATCC 15590
Acromobacter viscosus: ATCC 12448
Azotobacter chroococcum: ATCC 9043
Aeromonas punctata: ATCC 11163
Bacillus laterosporus: ATCC 64
Brevibacterium linens: ATCC 8377
Corynebacterium xerosis: ATCC 373
Citrobacter intermedius: IFO 13539
Cellulomonas flavigena: ATCC 15724
Erwinea carotovora: IFO 3380
Enterobacter agglomurans: ATCC 12287
Escherichia coli: ATCC 10798
Flavibacterium ferrugineum: ATCC 13524
Hafnia alvei: ATCC 9760
Kurthia zopfii: ATCC 6900
Klebsiella pneumoniae: ATCC 9621
Mycoplana bullata: ATCC 4278
Micrococcus varians: ATCC 399
Mi Microbacterium ammoniaphilum: ATCC 15354
Pseudomonas chlororaphis: ATCC 9446
Proteus mirabilis: ATCC 15290
Salmonella gallinarium: ATCC 9184
Seratia liquefaciens: ATCC 14460
Staphylococcus aureus: IFO 3060
Vibrio metschnikovii: ATCC 7708
Xanthomonas campestris: ATCC 8721
Zuglear ramigena: ATCC 19544
Protaminobacter alboflavus: IFO 3707
Thiobacillus perometabolis: ATCC 23370
Streptomyces olivaceus: IFO 3200
Nocardia corallina: IFO 3338
Candida lipolytica: IFO 0746
Cryptococcus neoformans: IFO 0608
Debaryomyces hansenii: IFO 0080
Deotrichum candidum: IFO 4602
Hansenula anomala: IFO 0122
Hanseniaspora valbyensis: IFO 0683
Kluyveromyces fragils: IFO 0541
Lipomyces lipofer: IFO 0673
Klokera japonica: IFO 0151
Pihia membranaefaciens: IFO 0460
Pachysolen tannophilus: IFO 1007
Rhodotorula glutinis: IFO 0395
Lodderomyces elongisporus: IFO 1676
Saccharomyces cerevisiae: IFO 2003
Trigonopsis variabilis: IFO 0755
Torulopsis famate: ATCC 12790

Usual culture media are used to obtain the cells of these microorganisms. When these culture media are cultivated with crotonbetaine added to them at the beginning or during the culture, the cells having good activity may be obtained.

Culture media used for cultivation of the microorganisms are usual ones containing usual carbon and nitrogen sources and inorganic ions, except that they contain crotonbetaine. When organic micronutrients such as vitamins and amino acids are further added, desirable results are obtained in many cases.

As carbon sources, carbohydrates such as glucose and sucrose, organic acids such as acetic acid, alcohols and the like are used properly, and as nitrogen sources, ammonia gas, ammonia water, ammonium salts and the like are used. As inorganic ions, magnesium ions, phosphoric ions, potassium ions, iron ions and the like are used properly, if necessary.

If the culture is carried out for 1 to 10 days under aerobic conditions while controlling the pH at an appropriate value in the pH range of 4 to 8 and the temperature is maintained at an appropriate value in the range of 25° to 40° C., desirable results can be obtained.

As the cells, culture broth itself after the completion of culture, cells separated from the culture broth and washed cells can all be used. As the treated cells, freeze dried cells; acetone dried cells; the cells brought into contact with toluene, surface active agents and the like; lysozyme-treated cells; cells exposed to ultrasonic waves and mechanically ground cells can be used. In addition, an enzyme protein fraction which has been obtained from treated cells and has an enzymatic activity for transforming crotonbetaine into L-carnitine, certain matter obtained from these cells and the insoluble matter of treated cells can all be used.

All of the foregoing microorganism-derived fractions have as a common feature the possession of active enzymes which are capable of bringing about the transformation of crotonbetaine into L-carnitine. Thus, by microorganism-derived fraction is meant one of the foregoing materials other than the whole, untreated microorganism which contains the necessary enzymes for said transformation.

As the aqueous media, water, buffers and those containing organic solvents such as ethanol can be used. Further, nutrients, anti-oxidants, surface active agents, coenzymes, hydroxylamine and metallic ions necessary for the growth of microorganisms can be added to the aqueous media, if necessary.

When cells of the above-mentioned microorganisms are brought into contact with crotonbetaine to act on it at the same time the cells are cultured in an aqueous medium, there is used an aqueous medium containing crotonbetaine and also nutrients such as carbon sources, nitrogen sources and inorganic ions which are necessary for the growth of microorganisms.

When organic micronutrients such as vitamins and amino acids are further added, desirable results are obtained in many cases.

As carbon sources, carbohydrates such as glucose and sucrose, organic acids such as acetic acid, alcohols and the like are used properly. As nitrogen sources, ammonia gas, ammonia water, ammonium salts and the like are used. As inorganic ions, magnesium ions, phosphoric ions, potassium ions, iron ions and the like are properly used, if necessary. If the culture is carried out under aerobic conditions controlling the pH at an appropriate value in the range of 4-8 and the temperature is maintained at an appropriate level in the range of 25°-40° C., desirable results can be obtained.

When the culture is carried out in this manner for 1 to 10 days, crotonbetaine is effectively transformed only into L-carnitine.

In contrast to the above method, when the culture broths themselves, cultured cells or treated cells of the above-mentioned microorganisms are brought into contact with crotonbetaine to act on it, it is sufficient to let an aqueous medium in which crotonbetaine and the culture broth, the cultured cells or the treated cells are dissolved or suspended sit on or stir with the aqueous medium for some time, controlling the temperature of the aqueous medium at an appropriate level in the range of 10°-70° C. and the pH of the aqueous medium at an appropriate value in the range of 4-8. When 5-100 hours elapse, a large amount of L-carnitine is formed and accumulated in the aqueous medium.

As methods for separating the thus obtained L-carnitine from the culture broth or the aqueous solution, usual methods are adopted such as a method with ion exchange resins and a precipitation method at an isoelectric point since there is no byproduct of D-carnitine with the method for producing L-carnitine of the present invention.

The formed L-carnitine was determined by the analytical method of David J. Poarson et al. (Refer to "Methods of Enzymatic Analysis", vol. 4 (2nd edition), page 1758, 1974, Academic Press Inc.)

The present invention will be described by Examples hereinafter.

EXAMPLE 1

50 ml of a mixed liquid containing 2 g/dl of glycerol, 0.3 g/dl of ammonium sulfate, 0.1 g/dl of $KH_2PO_4$, 0.3 g/dl of $K_2HPO_4$, 0.05 gldl of $MgSO_4.7H_2O$, 1 mg/dl of $FeSO_4.7H_2O$, 1 mg/dl of $MnSO_4.4H_2O$, 1 g/dl of an extract of yeast, 1 g/dl of peptone, 0.5 g/dl of an extract of maltose, 0.3 g/dl of crotonbetaine sulfate and 4.0 g/dl of calcium carbonate (separately sterilized) (pH 7.0) was placed in a 500 ml flask and the mixed liquid was sterilized at 120° C. for 15 minutes.

The mixed liquid was inoculated with a loop of *Acinetobacter lwoffi* ATCC 9036 or *Proteus mirabilis* ATCC 15290 that had been cultured in a nutrient agar at 30° C. for 30 hours and then cultured with shaking at 30° C. for 16 hours. The culture broth was centrifuged to separate the bacterial cells, which were once washed with the same volume of a physiological saline solution as that of the culture broth and then collected. The bacterial cells were added to a final volume of 100 ml of a 0.1M phosphoric acid buffer (pH 6.0) containing a 1.5 g/dl of crotonbetaine sulfate, and then the mixture was maintained at 30° C. for 16 hours for reaction between the bacterial cells and crotonbetaine.

The carnitine formed in the reaction liquid was determined by the above-mentioned enzymatic analytical method. As a result, 0.58 g/dl of L-carnitine was produced with *Acinetobacter lwoffi* ATCC 9036 and 0.53 g/dl of L-carnitine with *Proteus mirabilis* ATCC 15290. These reaction mixtures were centrifuged to separate bacterial cells, and then the supernatant clear liquids were ultrafiltered with a membrane having a molecular weight of 5000. Column chromatography with Dowex 50×12 was applied to the resulting filtrate. Carnitine was obtained as carnitine.HCl salt from carnitine fractions of the chromatography fractions. Measurement of the specific rotatory power of the carnitine verified that the carnitine was of the L configuration.

EXAMPLE 2

L-carnitine was formed by the same method as in Example 1 except for the use of microorganisms shown in Table 1. The amounts of formed L-carnitine in this case are shown in Table 1.

TABLE 1

| Microorganisms | | | L-carnitine formed (g/dl) |
|---|---|---|---|
| Alcaligenes marshallii | ATCC | 21030 | 0.44 |
| Aglobacterium tumefaciens | ATCC | 4452 | 0.39 |
| Arthrobacter paraffineus | ATCC | 15590 | 0.37 |
| Acromobacter viscosus | ATCC | 12448 | 0.37 |
| Azotobacter chroococcum | ATCC | 9043 | 0.16 |
| Aeromonas punctata | ATCC | 11163 | 0.17 |
| Bacillus laterosporus | ATCC | 64 | 0.32 |
| Brevibacterium linens | ATCC | 8377 | 0.49 |
| Corynebacterium xerosis | ATCC | 373 | 0.25 |
| Citrobacter intermudius | IFO | 13539 | 0.30 |
| Cellulomonas flavigena | ATCC | 15724 | 0.17 |
| Erwinea carotovora | IFO | 3380 | 0.31 |
| Enterobacter agglomerans | ATCC | 12287 | 0.36 |
| Escherichia coli | ATCC | 10798 | 0.55 |
| Flavibacterium ferrugineum | ATCC | 13524 | 0.57 |
| Hafnia alvei | ATCC | 9760 | 0.38 |
| Kurthia zopfii | ATCC | 6900 | 0.14 |
| Klebsiella pneumoniae | ATCC | 9621 | 0.21 |
| Mycoplana bullata | ATCC | 4278 | 0.47 |
| Micrococcus varians | ATCC | 399 | 0.32 |
| Microbacterium ammoniaphilum | ATCC | 15354 | 0.15 |
| Pseudomonas chlororaphis | ATCC | 9446 | 0.69 |
| Salmonella gallinarum | ATCC | 9184 | 0.26 |
| Seratia liquefaciens | ATCC | 14460 | 0.12 |
| Staphylococcus aureus | IFO | 3060 | 0.10 |
| Vibrio metschnikovii | ATCC | 7708 | 0.54 |
| Xanthomonas campestris | ATCC | 8721 | 0.35 |
| Zuglear ramigena | ATCC | 19544 | 0.11 |
| Protaminobacter alboflavus | IFO | 3707 | 0.14 |
| Streptomyces olivaceus | IFO | 3200 | 0.28 |
| Nocardia corallina | IFO | 3338 | 0.20 |
| Candida lipolytica | IFO | 0746 | 0.33 |
| Cryprococcus neoformans | IFO | 0608 | 0.17 |
| Debaryomyces hansenii | IFO | 0080 | 0.31 |
| Deotrichum candidum | IFO | 4602 | 0.29 |
| Hansenula anomala | IFO | 0122 | 0.18 |
| Hanseniaspora valbyensis | IFO | 0683 | 0.15 |
| Kluyveromyces fragils | IFO | 0541 | 0.14 |
| Lipomyces lipofer | IFO | 0673 | 0.14 |
| Klokera japonica | IFO | 0151 | 0.12 |
| Pihia membranaefaciens | IFO | 0460 | 0.24 |
| Pachysolen tannophilus | IFO | 1007 | 0.11 |
| Rhodotorula glutinis | IFO | 0395 | 0.18 |
| Lodderomyces elongisporus | IFO | 1676 | 0.15 |
| Saccharomyces cerevisiae | IFO | 2003 | 0.29 |
| Trigonopsis variabilis | IFO | 0755 | 0.32 |
| Torulopsis famata | ATCC | 12790 | 0.15 |

EXAMPLE 3

The same culture medium as in Example 1 except that crotonbetaine was inoculated with a loop of *Acinetobacter lwoffi* ATCC 9036 which had been cultured in a nutrient agar at 30° C. for 30 hours and then cultured with shaking at 30° C. for 12 hours. After that, 5 ml of a solution containing 15 g/dl of crotonbetaine sulfate (which had been neutralized to a pH value of 6.0 with KOH) was added to the culture broth, and then the culture broth was further cultured at 30° C. for 10 hours. The amount of L-carnitine formed in the final culture broth was determined by the same analytical method as in Example 1, and, as a result, it was verified that 0.43 g/dl of L-carnitine was formed.

EXAMPLE 4

*Acinetobacter lwoffi* ATCC 9036 was cultured by the same method as in Example 1, and then bacterial cells of the culture broth were separated, washed and then collected by the same method as in Example 1. The collected bacterial cells were dispersed in the physiological saline solution to prepare 5 ml of a bacterial suspension containing 20 g/dl of bacterial cells. 5 ml of 4% solution of sodium alginate was added to 5 ml of the bacterial suspension to prepare a mixed liquid, and then an aqueous solution containing 15 g/dl of calcium chloride was added dropwise to the mixed liquid to prepare bead-shaped immobilized bacterial cells. The total amount of the immobilized bacterial cells was placed into 20 ml of 0.1M phosphoric acid buffer (pH 6.0) containing 1.5 g/dl of crotonbetaine sulfate, and then the mixture was maintained at 30° C. for 5 hours to allow reaction between the bacterial cells and crotonbetaine. As a result, 0.34 g/dl of L-carnitine was formed in the reaction liquid.

EXAMPLE 5

L-carnitine was formed using *Acinetobacter lwoffi* ATCC 9036 by the same method as in Example 1 except for the addition of metal ions shown in Table 2 to the reaction liquid.

The results are shown in Table 2.

TABLE 2

| Metal ions added (5 mM) | L-carnitine formed (g/dl) |
|---|---|
| None | 0.56 |
| LiCl | 0.67 |
| FeSO$_4$.7H$_2$O | 0.76 |
| MnSO$_4$.4H$_2$O | 0.72 |
| CoCl$_2$.6H$_2$O | 0.72 |
| ZnSO$_4$.7H$_2$O | 0.73 |
| CuSO$_4$.5H$_2$O | 0.82 |
| MgSO$_4$.7H$_2$O | 0.82 |
| NiCl$_2$.6H$_2$O | 0.81 |
| CaCl$_2$.2H$_2$O | 0.71 |
| BaCl$_2$ | 0.83 |
| Cr$_2$(SO$_4$)$_3$ | 0.89 |
| Na$_2$MoO$_4$.2H$_2$O | 0.83 |

EXAMPLE 6

L-carnitine was formed by the same process as in Example 3 except the use of crotonbetaine instead of crotonbetaine sulfate. As a result, 0.74 g/dl of L-carnitine was formed.

What is claimed as new and desired to be secured by Letters Patent of the United States is:

1. A method for producing L-carnitine, which comprises:
    contacting crotonbetaine or a salt thereof and a microorganism or microorganism-derived fraction which is competent to transform crotonbetaine or salts thereof into L-carnitine in an aqueous medium under conditions suitable for the formation of L-carnitine, and
    recovering L-carnitine,
    wherein the microorganism is selected from the group consisting of:
    Alcaligenes marshallii: ATCC 21030,
    Acinetobacter lwoffi: ATCC 9036,
    Aglobacterium tumefaciens: ATCC 4452,
    Arthrobacter parraffineus: ATCC 15590,
    Acromobacter viscosus: ATCC 12448,
    Azotobacter chroococcum: ATCC 9043,
    Aeromonas punctata: ATCC 11163,
    Bacillus laterosporus: ATCC 64,
    Brevibacterium linens: ATCC 8377,
    Corynebacterium xerosis: ATCC 373,

*Citrobacter intermedius:* IFO 13539,
*Cellulomonas flavigena:* ATCC 15724,
*Erwinea carotovora:* IFO 3380,
*Enterobacter agglomurans:* ATCC 12287
*Flavibacterium ferrugineum:* ATCC 13524,
*Hafnia alvei:* ATCC 9760,
*Kurthia zopfii:* ATCC 6900,
*Klebsiella pneumoniae:* ATCC 9621,
*Mycoplana bullata:* ATCC 4278,
*Micrococcus varians:* ATCC 399,
*Microbacterium ammoniaphilum:* ATCC 15354,
*Pseudomonas chlororaphis:* ATCC 9446,
*Proteus mirabilis:* ATCC 15290,
*Salmonella gallinarum:* ATCC 9184,
*Seratia liquefaciens:* ATCC 14460,
*Staphylococcus aureus:* IFO 3060,
*Vibrio metschnikovii:* ATCC 7708,
*Xanthomonas campestris:* ATCC 8721,
*Zuglear ramigena:* ATCC 19544,
*Protaminobacter alboflavus:* IFO 3707,
*Thiobacillus perometabolis:* ATCC 23370,
*Streptomyces olivaceus:* IFO 3200,
*Nocardia corallina:* IFO 3338,
*Candida lipolytica:* IFO 0746,
*Cryptococcus neoformans:* IFO 0608,
*Debaryomyces hansenii:* IFO 0080,
*Deotrichum candidum:* IFO 4602,
*Hansenula anomala:* IFO 0122,
*Hanseniaspora valbyensis:* IFO 0683,
*Kluyveromyces fragils:* IFO 0541,
*Lipomyces lipofer:* IFO 0673,
*Klokera japonica:* IFO 0151,
*Pihia membranaefaciens:* IFO 0460,
*Pachysolen tannophilus:* IFO 1007,
*Rhodotorula glutinis:* IFO 0395,
*Lodderomyces elongisporus:* IFO 1676,
*Saccharomyces cerevisiae:* IFO 2003,
*Trigonopsis variabilis:* IFO 0755, and
*Torulopsis famate:* ATCC 12790.

2. The method of claim 1 wherein the non-toxic, soluble salt of crotonbetaine is sulfate.

3. The method of claim 1 wherein said medium further comprises one or more salts selected from the group consisting of: LiCl, $FeSO_4.7H_2O$, $MnSO_4.4H_2O$, $CoCl_2.6H_2O$, $ZnSOi_4.7H_2O$, $CuSO_4.5H_2O$, $MgSO_4.7H_2O$, $NiCl_2.6H_2O$, $CaCl_2.2H_2O$, $BaCl_2$, $Cr_2(SO_4)_3$, and $Na_2MoO_4.2H_2O$.

4. The method of claim 1 wherein the L-carnitine is produced under aerobic conditions, at a pH in the range of 4 to 8, at a temperature of from 10° C. to 70° C. and the L-carnitine is collected after 5 to 240 hours.

5. The method of claim 4 wherein the L-carnitine is collected after 24 to 240 hours.

6. The method of claim 5 wherein the temperature is from 25° C. to 40° C.

* * * * *